(12) United States Patent
McDevitt et al.

(10) Patent No.: US 6,302,886 B1
(45) Date of Patent: Oct. 16, 2001

(54) METHOD AND APPARATUS FOR PREVENTING MIGRATION OF SUTURES THROUGH TRANSOSSEOUS TUNNELS

(75) Inventors: Dennis McDevitt, Upton; James Nicholson, Lincoln, both of MA (US)

(73) Assignee: Innovasive Devices, Inc., Marlborough, MA (US)

( * ) Notice: Subject to any disclaimer, the term of this patent is extended or adjusted under 35 U.S.C. 154(b) by 0 days.

(21) Appl. No.: 09/234,022

(22) Filed: Jan. 19, 1999

Related U.S. Application Data

(63) Continuation of application No. 08/689,443, filed on Aug. 9, 1996, now Pat. No. 5,860,978, which is a continuation-in-part of application No. 08/163,130, filed on Dec. 6, 1993, now Pat. No. 5,725,529, which is a continuation-in-part of application No. 07/765,445, filed on Sep. 25, 1991, now Pat. No. 5,268,001, which is a continuation-in-part of application No. 07/588,055, filed on Sep. 24, 1990, now Pat. No. 5,088,147.

(51) Int. Cl.[7] .................................................. A61B 17/56
(52) U.S. Cl. .................................. 606/72; 606/232; 623/13
(58) Field of Search .................................. 606/72, 73, 80, 606/86, 87, 88; 623/13

(56) References Cited

U.S. PATENT DOCUMENTS

| Re. 34,293 | 6/1993 | Goble et al. . |
|---|---|---|
| 2,381,050 | 8/1945 | Hardinge . |
| 3,036,482 | 5/1962 | Kenworthy et al. . |
| 3,566,739 | 3/1971 | Lebar . |
| 3,708,883 | 1/1973 | Flander . |

(List continued on next page.)

FOREIGN PATENT DOCUMENTS

| 31 46634 | 6/1983 | (DE) . |
|---|---|---|
| 34 06961 | 9/1985 | (DE) . |
| 85 20206 | 6/1986 | (DE) . |
| 0 058 744 | 9/1982 | (EP) . |
| 0 124 489 | 11/1984 | (EP) . |

(List continued on next page.)

OTHER PUBLICATIONS

Abrams, Jeffrey S. "Arthroscopic Assisted Rotator Cuff Repairs." *Arthroscopic Surgery of the Shoulder*. 13th Annual San Diego Meeting, 6/95, pp. 151–154 & 164.

Bigliani, Louis U., Ticker, Jonathan B., flatow, Evan L., Soslowsky, Louis J. and Mow, Van C. "The Relationship of Acromial Architecture to Rotator Cuff Disease." *Clinics in Sports Medicine*. 10 No. 4(1991) pp. 823–838.

* Craft, et al. "Fixation Strength of Rotator Cuff Repairs With Suture Anchors and the Transosseous Suture Technique." *Journal of Shoulder and Elbow Surgery*. 5, No. 1(1996), pp. 32–40.

* Ellman, Harvard, Hanker, Gregory and Bayer, Michael. "Repair of the Rotator Cuff." *The Journal of Bone and Joint Surgery*. 68–A No. 8 (1986) pp. 1136–1144.

* France, E. Paul, Paulos, Lonnie E., Harner, Chris D. and Straight, Chris B. Biomechanical Evaluation of Rotator Cuff Fixation Methods. *The American Journal of Sports Medicine*. 17 No. 2(1989) pp. 176–181.

(List continued on next page.)

*Primary Examiner*—Michael A. Brown
(74) *Attorney, Agent, or Firm*—Choate, Hall & Stewart

(57) ABSTRACT

An improved method for attaching soft tissue to bone by passing a suture through an opening in the bone, e.g., a transosseous tunnel, and affixing the soft tissue with the suture. The improvement, for preventing the suture from migrating through the bone at the end of the opening, includes placing a eyelet into an end of the bone opening and passing the suture through the eyelet, as well as through the opening in the bone, in order to affix the soft tissue to the bone with the suture.

8 Claims, 9 Drawing Sheets

U.S. PATENT DOCUMENTS

| | | |
|---|---|---|
| 3,842,824 | 10/1974 | Neufeld . |
| 3,953,896 * | 5/1976 | Treace ................................... 623/13 |
| 3,973,277 * | 8/1976 | Semple et al. ......................... 623/13 |
| 4,013,071 | 3/1977 | Rosenberg . |
| 4,091,806 | 5/1978 | Aginsky . |
| 4,149,277 * | 4/1979 | Bokros ................................... 623/13 |
| 4,408,938 | 10/1983 | Maguire . |
| 4,492,226 | 1/1985 | Belykh et al. . |
| 4,506,670 | 3/1985 | Crossley . |
| 4,590,928 | 5/1986 | Hunt et al. . |
| 4,632,100 | 12/1986 | Somers et al. . |
| 4,716,893 | 1/1988 | Fischer et al. . |
| 4,738,255 | 4/1988 | Goble . |
| 4,741,330 | 5/1988 | Hayhurst . |
| 4,744,793 | 5/1988 | Parr . |
| 4,778,468 | 10/1988 | Hunt et al. . |
| 4,828,562 | 5/1989 | Kenna . |
| 4,870,957 | 10/1989 | Goble . |
| 4,871,289 | 10/1989 | Choiniere . |
| 4,873,976 | 10/1989 | Schreiber . |
| 4,894,063 | 1/1990 | Nashef . |
| 4,940,467 | 7/1990 | Tronzo . |
| 4,944,742 | 7/1990 | Clemow et al. . |
| 5,013,316 | 5/1991 | Goble et al. . |
| 5,037,422 | 8/1991 | Hayhurst et al. . |
| 5,046,513 | 9/1991 | Gatturna et al. . |
| 5,108,431 * | 4/1992 | Mansat et al. ......................... 623/13 |
| 5,116,337 | 5/1992 | Johnson . |
| 5,141,373 | 8/1992 | Kendall . |
| 5,141,520 | 8/1992 | Goble et al. . |
| 5,152,763 | 10/1992 | Johnson . |
| 5,176,682 | 1/1993 | Chow . |
| 5,207,679 | 5/1993 | Li . |
| 5,209,753 | 5/1993 | Biedermann et al. . |
| 5,224,946 | 7/1993 | Hayhurst et al. . |
| 5,236,445 | 8/1993 | Hayhurst et al. . |
| 5,248,231 | 9/1993 | Denham et al. . |
| 5,258,015 | 11/1993 | Li et al. . |
| 5,268,001 | 12/1993 | Nicholson et al. . |
| 5,324,308 | 6/1994 | Pierce . |
| 5,326,205 | 7/1994 | Anspach, Jr. et al. . |
| 5,354,298 | 10/1994 | Lee et al. . |
| 5,411,523 | 5/1995 | Goble . |
| 5,417,712 | 5/1995 | Whittaker . |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,496,326 | 3/1996 | Johnson . |
| 5,501,683 | 3/1996 | Trott . |
| 5,501,695 | 3/1996 | Anspach et al. . |
| 5,522,845 | 6/1996 | Wenstrom, Jr. . |
| 5,540,703 | 7/1996 | Barker, Jr. et al. . |
| 5,545,180 | 8/1996 | Le et al. . |
| 5,571,104 | 11/1996 | Li . |

FOREIGN PATENT DOCUMENTS

| | | |
|---|---|---|
| 0 232 049 | 8/1987 | (EP) . |
| 0 241 240 | 10/1987 | (EP) . |
| 0 260 970 | 3/1988 | (EP) . |
| 0 270 704 | 6/1988 | (EP) . |
| 0 251 583 | 7/1988 | (EP) . |
| 0 340 159 | 11/1989 | (EP) . |
| 0 409 364 | 1/1991 | (EP) . |
| 0 574 707 | 12/1993 | (EP) . |
| 2.054.731 | 5/1971 | (FR) . |
| 2 346 591 | 10/1977 | (FR) . |
| 2 622 430 | 5/1989 | (FR) . |
| 2 084 468 | 4/1982 | (GB) . |
| 89/01767 | 3/1989 | (WO) . |
| 92/04874 | 4/1992 | (WO) . |
| 92/10149 | 6/1992 | (WO) . |
| 95/15726 | 6/1995 | (WO) . |
| 88/09157 | 12/1998 | (WO) . |

OTHER PUBLICATIONS

* Gerber, Christian, Schneeberger, Alberto G., Beck, Martin and Schlegel, Urs. "Mechanical Strength of Repairs of the Rotator Cuff." *The Journal of Bone and Joint Surgery*. 76–B No. 3(1994) pp. 371–380.

* Reed, Stephen C., Glossop, N. and Ogilvie–Harris, Darrell J. "Full–Thickness Rotator Cuff Tears—A Biomechanical Comparison of Suture Versus Bone Anchor Techniques." *The American Journal of Sports Medicine*. 24 No. 1(1996) pp. 46–481.

* cited by examiner

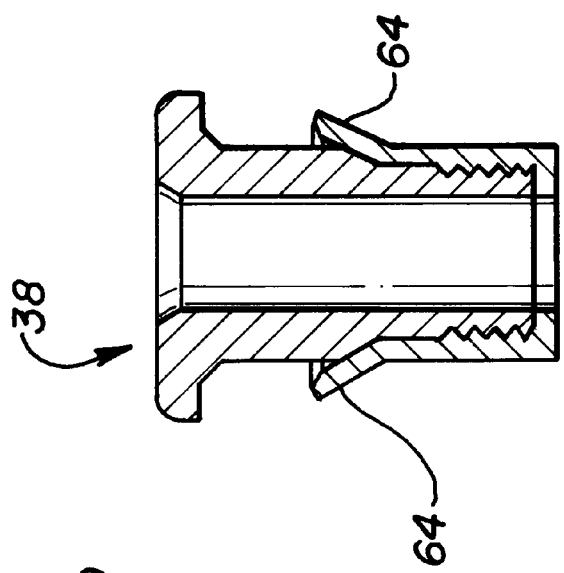
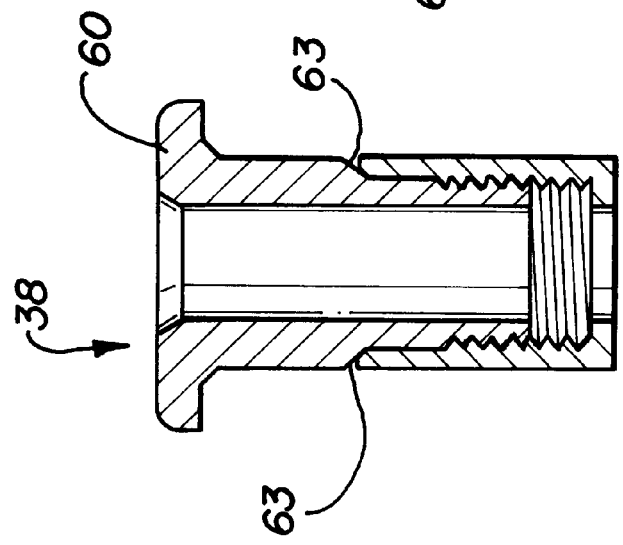
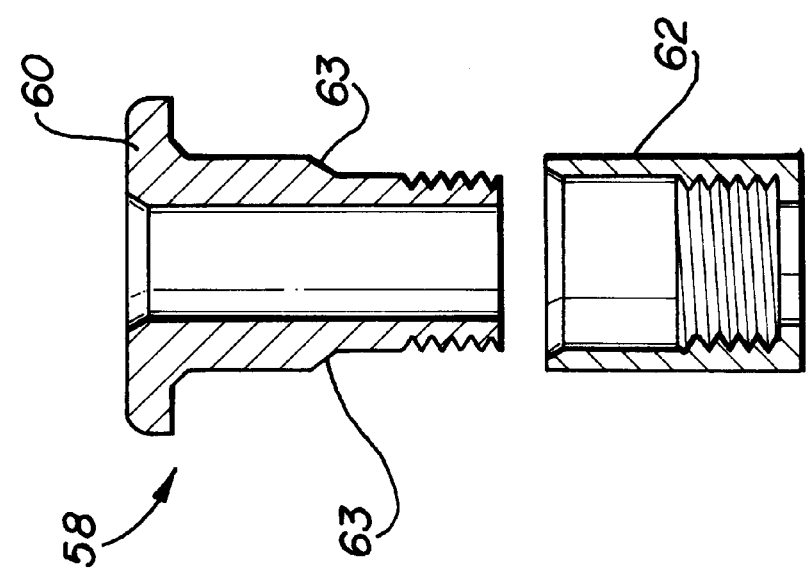

METHOD AND APPARATUS FOR PREVENTING MIGRATION OF SUTURES THROUGH TRANSOSSEOUS TUNNELS

This application is a continuation of U.S. application Ser. No. 08/689,443, filed Aug. 9, 1996, now U.S. Pat. No. 5,860,978 which is a continuation-in-part of U.S. application Ser. No. 08/163,130, filed Dec. 6, 1993, now U.S. Pat. No. 5,725,529 which is a continuation-in-part of U.S. application Ser. No. 07/765,445, filed Sep. 25, 1991, and issued as U.S. Pat. No. 5,268,001, which is a continuation-in-part of U.S. patent application Ser. No. 07/588,055, filed Sep. 24, 1990, now U.S. Pat. No. 5,088,147. The entire contents of these applications are incorporated herein by reference.

BACKGROUND OF THE INVENTION

This invention pertains to surgical systems and, more particularly, methods and apparatus for attaching tissue to bone. The invention has application in, for example, rotator cuff repair.

It is not uncommon for tendons and other soft tissues to tear or to detach from bone. Athletes, for example, often suffer "rotator cuff" tears, in which the supraspinatus tendon separates from the humerus, causing pain and loss of ability to elevate and externally rotate the arm. Complete separation can occur if the shoulder is subjected to gross trauma. Typically, however, the tear begins as a small lesion, especially, in older patients.

To repair a torn rotator cuff, surgeons must reattach the supraspinatus tendon to the humerus. Traditionally, this has been done by boring several holes obliquely through the greater tuberosity, that is, the bony structure on the outer side of the head of the humerus. Sutures are then passed through these holes, or transosseous tunnels, in order to secure the tendon.

Though use of such sutures to anchor the tendon have been referred to as the "gold standard," it has been shown that the sutures migrate through the bone itself, particularly, along the upper edge of the openings that define the ends of transosseous tunnels on lateral cortex of the greater tuberosity. This is particularly pronounced in older patients, whose bone structures tend to be weaker and, therefore, less resistant to degradation under the force of the sutures. On prior art solution has been to augment the edges of the transosseous tunnels by affixing plate-like pieces; see, Gerber et al, "Mechanical Strength of Repairs of the Rotator Cuff," *Journal of Bone Joint Surgery*, v. 76, n. 3, p. 371–380 (May 1994). See France et al, "Biomechanical Evaluation of Rotator Cuff Fixation Methods," *The American Journal of Sports Medicine*. v. 17. n. 2. pp. 176 et seq.

Drawbacks of plate-like augmentation of the greater tuberosity are the difficulties in positioning and affixing the plates. Though endoscopic surgery is generally preferred, use of augmentation plates necessitates that rotator cuff repair be performed by open surgery. Moreover, the plates must be affixed to the bone by surgical glues in order to avoid risk that they will migrate from the site in the event of suture breakage.

An object of this invention is to provide improved surgical systems and, more particularly, methods and apparatus for attaching tissue to bone.

Another object of this invention is to provide improved methods and apparatus for rotator cuff repair.

A related object of the invention is to provide improved methods for reinforcing the edges of transosseous tunnels against force of sutures.

SUMMARY OF THE INVENTION

The above objects are among those met by the invention, which provides in one aspect an improvement on a method for attaching soft tissue to bone by passing a suture through an opening in the bone, e.g., a transosseous tunnel, and affixing the soft tissue with the suture. The improvement, for preventing the suture from migrating through the bone at the end of the opening, includes placing an eyelet into an end of the bone opening and passing the suture through the eyelet, as well as through the opening in the bone, in order to affix the soft tissue with the suture.

In a related aspect, the invention provides a method as described above for use in attaching the spinatus tendon to the humerus bone by placing an eyelet into an end of a transosseous tunnel and passing the suture through the eyelet, as well as through the tunnel, in order to affix the tendon to the humerus.

Further aspects of the invention provide methods as described above, in which the eyelet is screwed, or fit by interference, into the bone opening. In still further related aspects, the bone opening is expanded prior to placement of the eyelet.

In another aspect, the invention provides an apparatus for use in rotator cuff repair for reinforcing a trnsosseous tunnel to prevent migration of a suture through bone at the end of the tunnel. The apparatus comprises an eyelet arranged for placement within the end of the tunnel, or within an expanded hole formed at the end of the tunnel. The eyelet has a channel therethrough for passage of the suture and can include a flanged head to prevent the eyelet from being forced too far into the tunnel.

Related aspects of the invention provide an apparatus as described above in which the eyelet is threaded for screwing into bone on the inside of the wall of the hole or, alternatively, is arranged for interference fit with that inside wall.

Still another aspect of the invention provides an improvement on a method for attaching soft tissue to bone by passing a suture through an opening in the bone and affixing the soft tissue with the suture. The improvement, for reinforcing the bone opening, includes placing an expandable member into an end of the bone opening and inserting an insertion element into a channel that passes through the expandable member. A portion of the insertion element has an outer diameter greater than an inner diameter of at least a portion of the channel in the expandable member, so that insertion of the insertion element into the expandable member causes the expandable member to expand to obtain a pressure fit with the bone opening. The improvement further includes passing the suture through an channel of the insertion element, as well as through the opening in the bone, in order to affix the soft tissue with the suture.

Another aspect of the invention provides a method as described above in which the expandable member is substantially cylindrical and has an axial channel that extends between its proximal and distal ends. According to this embodiment, the insertion element is likewise elongate and has an axial channel extending between its proximal and distal ends.

In yet another aspect, the methods described above are adapted for rotator cuff repair. Accordingly, the step of placing the expandable member into the end of the bone opening comprises placing that member into the end of a transosseous tunnel in the humerus.

Yet another aspect of the invention provides methods as described above in which an emplacement element is used to place an expandable member into the end of the bone opening. In a related aspects, the emplacement element is frangibly attached to the expandable member such that application of force to the insertion element breaks the frangible attachment between those elements after that force has caused the insertion element to expand the expandable member.

Advantages of the invention include the ability to install the reinforcing eyelet via endoscopic surgery, as well as open surgery.

These and other aspects of the invention are evident in the drawings and in the description that follows.

BRIEF DESCRIPTION OF THE DRAWINGS

A more complete understanding of the invention may be attained by reference to the drawings, in which:

FIGS. 4–7 depict further eyelets according to the invention.

DETAILED DESCRIPTION OF THE ILLUSTRATED EMBODIMENT

Figure 1A:
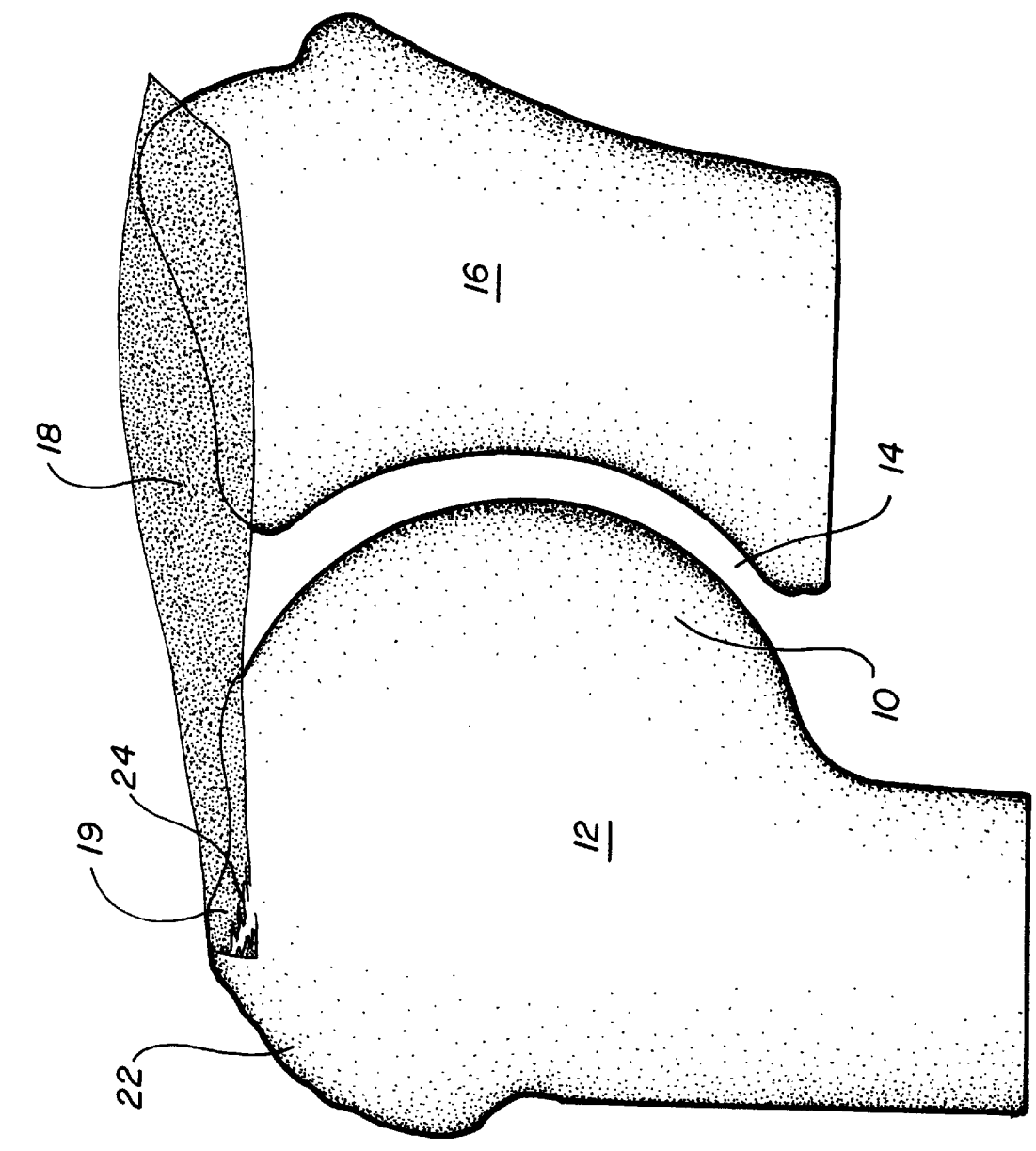
FIG. 1A depicts a partially torn rotator cuff.
Figure 1B:
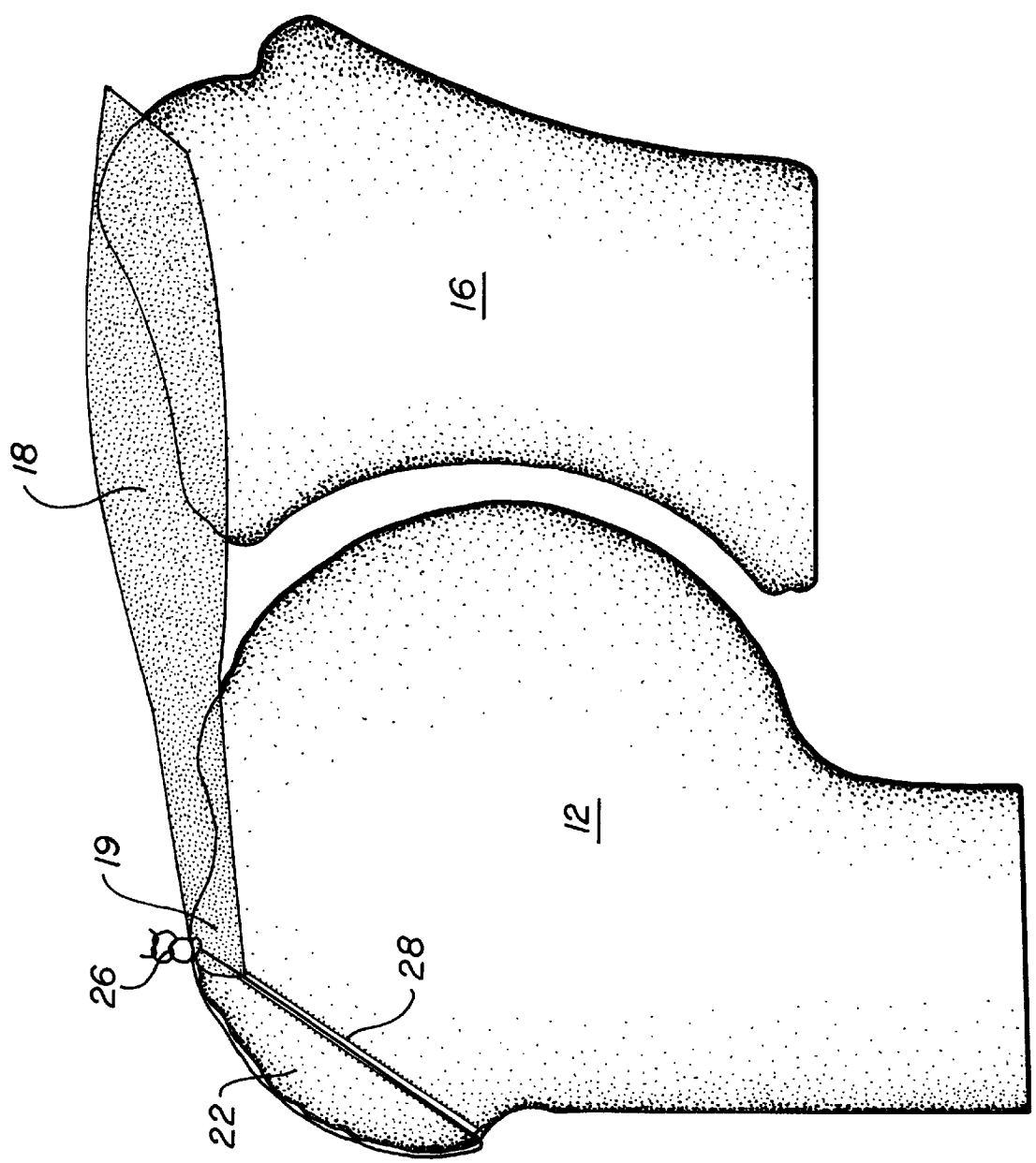
FIG. 1B depicts the rotator cuff of FIG. 1A repaired in accord with prior art surgical techniques.

FIG. 1A depicts a partially torn rotator cuff. In the illustration, the globular head 10 of humerus 12 rests in the glenoid cavity 14 formed by the scapula 16. The supraspinatus muscle 18 traverses the scapular spine (not shown) and converges into a tendon 19 (undifferentiated in the illustration), the end of which is normally fully inserted into a facet of the greater tuberosity 22. A partial tear rotator cuff results when a portion 24 of the tendon 19 detaches from the greater tuberosity 22, as shown in the illustration FIG. 1B illustrates the rotator cuff of FIG. 1A repaired in accord with the prior art suturing technique, in which the tendon 19 is resecured to the humerus by a suture 26 passed through a transosseous tunnel 28 bored obliquely through the greater tuberosity 22. A further understanding of the prior art suturing technique may be attained by reference to Gerber, et al, "Mechanical Strength of Repairs of the Rotator Cuff," *Journal of Bone and Joint Surgery*, v. 76-B, no. 3 (May 1994), at pp. 371, et seq., the teachings of which are incorporated herein by reference.

Though FIG. 1B shows use of only a single transosseous tunnel and suture, multiple tunnels and sutures are typically used, as discussed in the aforementioned prior art reference. Each suture can be looped superiorly (i.e., over the greater tuberosity), passed through the tendon and tied to itself Alternatively, pairs of adjacent sutures can be tied together between the exit holes on the lateral cortex.

Figure 2:
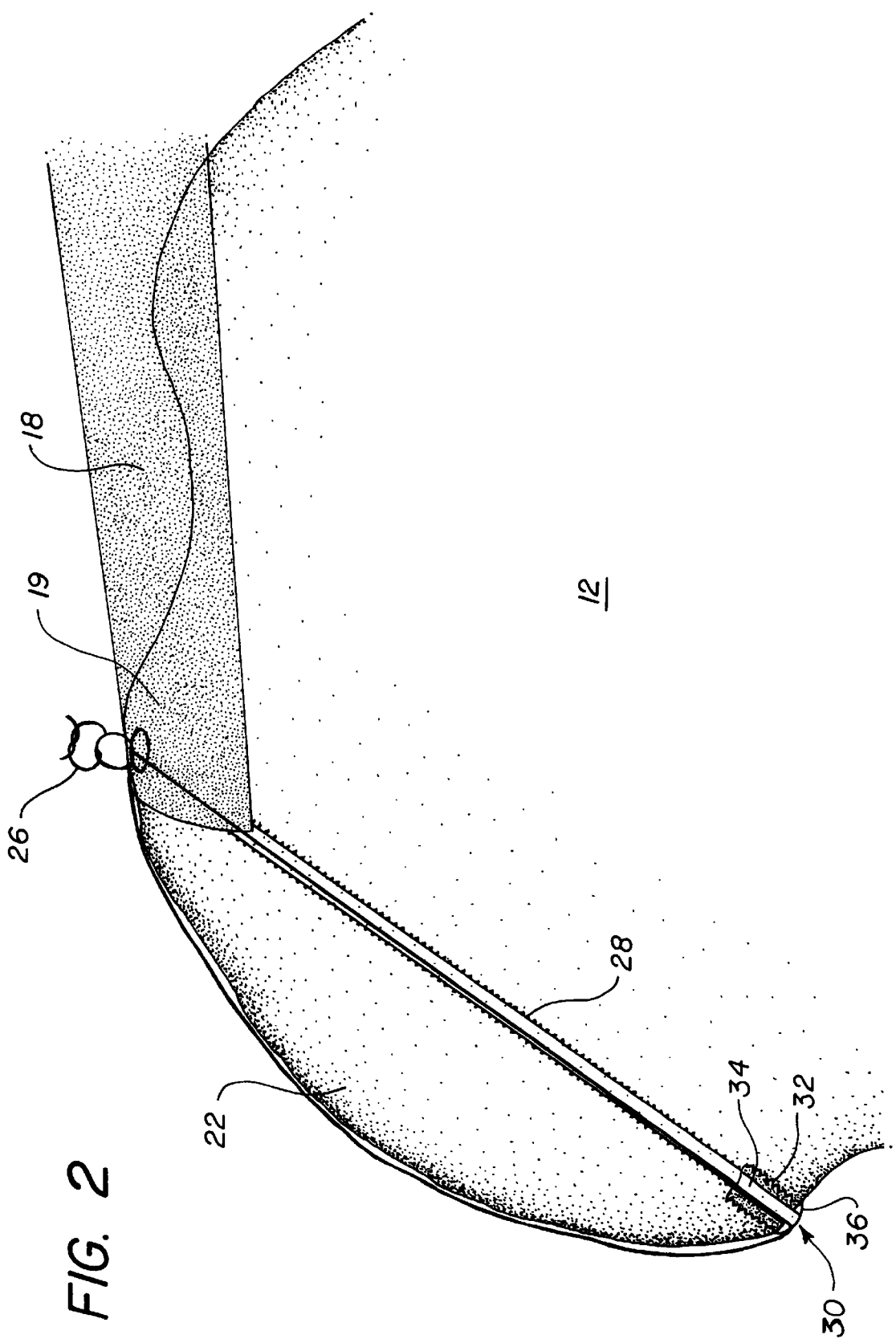
FIG. 2 depicts a surgical rotator cuff repaired according to the invention.

FIG. 2 illustrates a modified suturing technique according to the invention. The modification comprises use of a bone "eyelet" to reinforce the opening 30 at the end of transosseous tunnel 28 on the lateral cortex of the greater tuberosity 22. This prevents migration of the suture 26 through the upper edoe of the opening 30. Such migration has been discovered to result from repeated loading of the suture during use of the shoulder.

The eyelet 32 comprises a cylinder, or other such solid geometric shape (e.g., parallelapiped), suitable to be embedded into the humerus 12 and, particularly, the greater tuberosity 22, as shown. The eyelet 32 includes a cannula 34, which is aligned with the transosseous tunnel 28, through which suture 26 passes. The eyelet 32 also preferably includes a head 36 that protrudes above the bone surface. This head 36 is flanged to prevent the eyelet 32 from being driven too far into the opening 30 and, more particularly, to prevent the head from being driven below the bone surface on emplacement or as a result of forces exerted by the suture 26.

The eyelet 32 is threaded into transosseous tunnel 28 or is held by interference fit, surgical epoxy or, simply, by the force exerted by suture 26. In instances where the eyelet 32 requires it, the end 30 of the tunnel 28 can be enlarged to facilitate embedding the eyelet in the bone.

The eyelet 32 is comprised of a biocompatible material, i.e., a material that is chemically and biologically inert, such as, an implant grade high density polyethylene, low density polyethylene (PE 6010 and PE 2030) and polypropylene (13R9A and 23M2: all made by Rexene, Dallas, Tex.). The eyelet 32 may also be comprised of a metal, such as, surgical implant grade stainless steel.

In one preferred embodiment, an eyelet 40 according to the invention is constructed in a manner similar to the bone anchor of the type described in copending, commonly assigned U.S. application patent application Ser. No. 08/163, 130, filed Dec. 6, 1993, the teachings of which are incorporated herein by reference. Such an eyelet is illustrated in FIGS. 3A–3E.

Figure 3A:
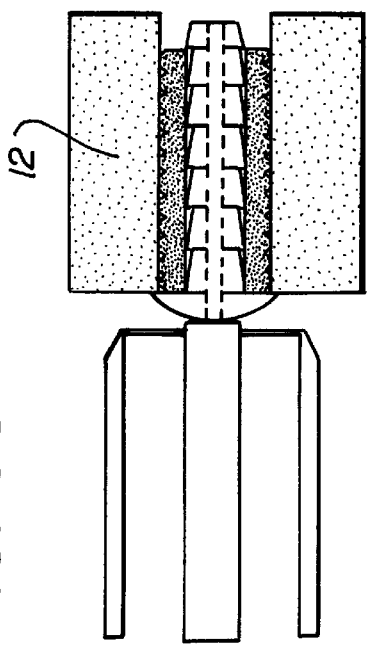
FIGS. 3A–3E depict an eyelet according to the invention and its use in rotator cuff repair according to the invention.

Referring to FIG. 3A, the eyelet 40 generally comprises an elongated insertion element 42 and an approximately cylindrical expandable member 44. In its unexpended state, the expandable member 44 can be placed into a bone hole 45, i.e., the end 30 of the transosseous tunnel 28 or an enlarged opening drilled into the bone at the end 30 of the tunnel 28. The expandable member 44 includes an axial channel 46, running end to end, for receiving the insertion element and for permitting passage of a transosseous suture.

As shown in the drawing, the outer diameter of at least a portion of the insertion element 42 is greater than the inner diameter of at least a portion of the axial channel 46 of the expandable member 44. Accordingly, when the insertion element 42 is inserted into the axial channel 46, the wider portion of the insertion element 42 exerts on the walls of the expandable member 44 a force orthogonal to the channel 46. This outward force causes the expandable member 44 to expand against the walls of bone hole 45, fixing the insertion element 42 within the expandable member 44 and fixing the expandable member 44 in a pressure fit firmly within the opening 45.

The expandable member 44 includes an outer surface for secured engagement with an inner surface of the tansosseous tunnel. That outer surface can be smooth or can be provided with a plurality of ridges 48, as shown. In particular, a preferred configuration includes a plurality of annular ridges for engaging irregularities in the bone opening wall as the expandable member 44 deforms and conforms to the bone opening wall during and after expansion.

The expandable member 44 also includes a flanged head 49 disposed at the end to prevent the member 44 from being driven too far into the transosseous tunnel on emplacement or as a result of forces exerted by the transosseous suture. The head 49 preferably has a rounded outer surface to better distribute loads placed on it by the suture.

The insertion element 42 is a substantially elongated shape with an outer surface having one or more projections 50 for engagement with the inner surface of the axial channel 46 of expandable member 44. The projections 50 include portions with outer diameters that are greater than the inner diameter of the channel 46, as shown, so that they expand the expandable member 44 upon insertion.

The insertion element 42 includes a channel 52 running the length of the element, from end to end. The channel is sized to permit passage of a suture 26 of the type used for transosseous suture repair of the rotator cuff.

The eyelet 40 is embedded in the transosseous tunnel 28 45 using an emplacement device of the type disclosed in aforementioned U.S. application patent application Ser. No. 08/163,130. The device includes a cylindrical holding member 54 that holds the expandable member during emplacement via a frangible junction 55. The holding member also retains the insertion element 42 in alignment with the end of the expandable member 44, as shown. The emplacement device further includes a plunger 56 that exerts force on the insertion element 42 forcing it into the frangibly-retained expandable member 44 and causing the holding member to break-away from the expandable member 44, once insertion is complete.

A further understanding of the construction and operation of a bone anchor upon which the eyelet 40 is based may be attached by reference to aforementioned U.S. application patent application Ser. No. 08/163,130, the teachings of which are incorporated herein by reference.

Figure 3B:
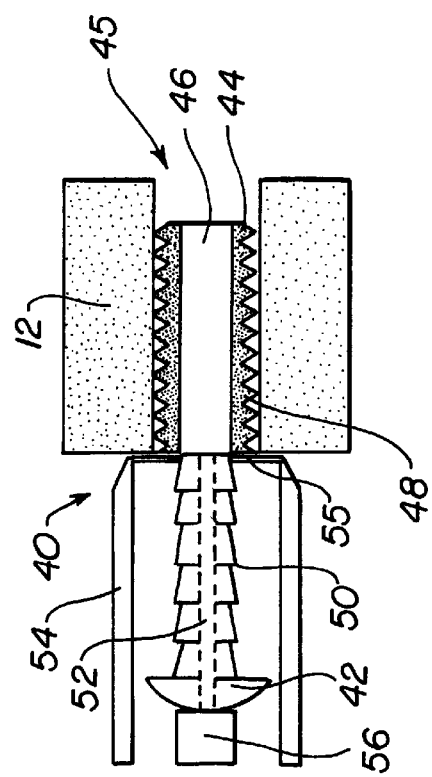
Figure 3C:
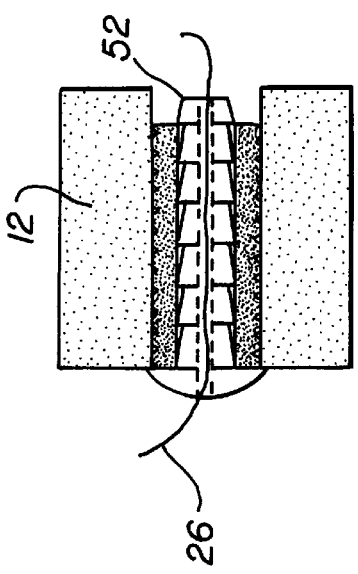
Figure 3D:
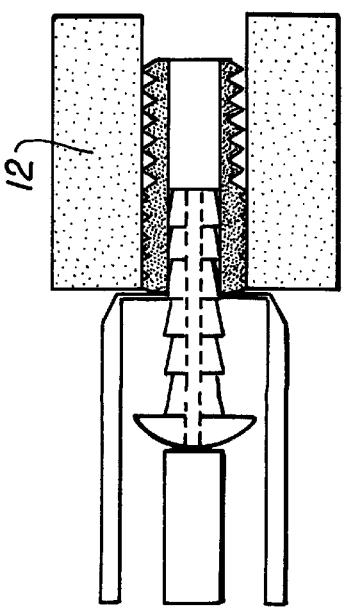
Figure 3E:
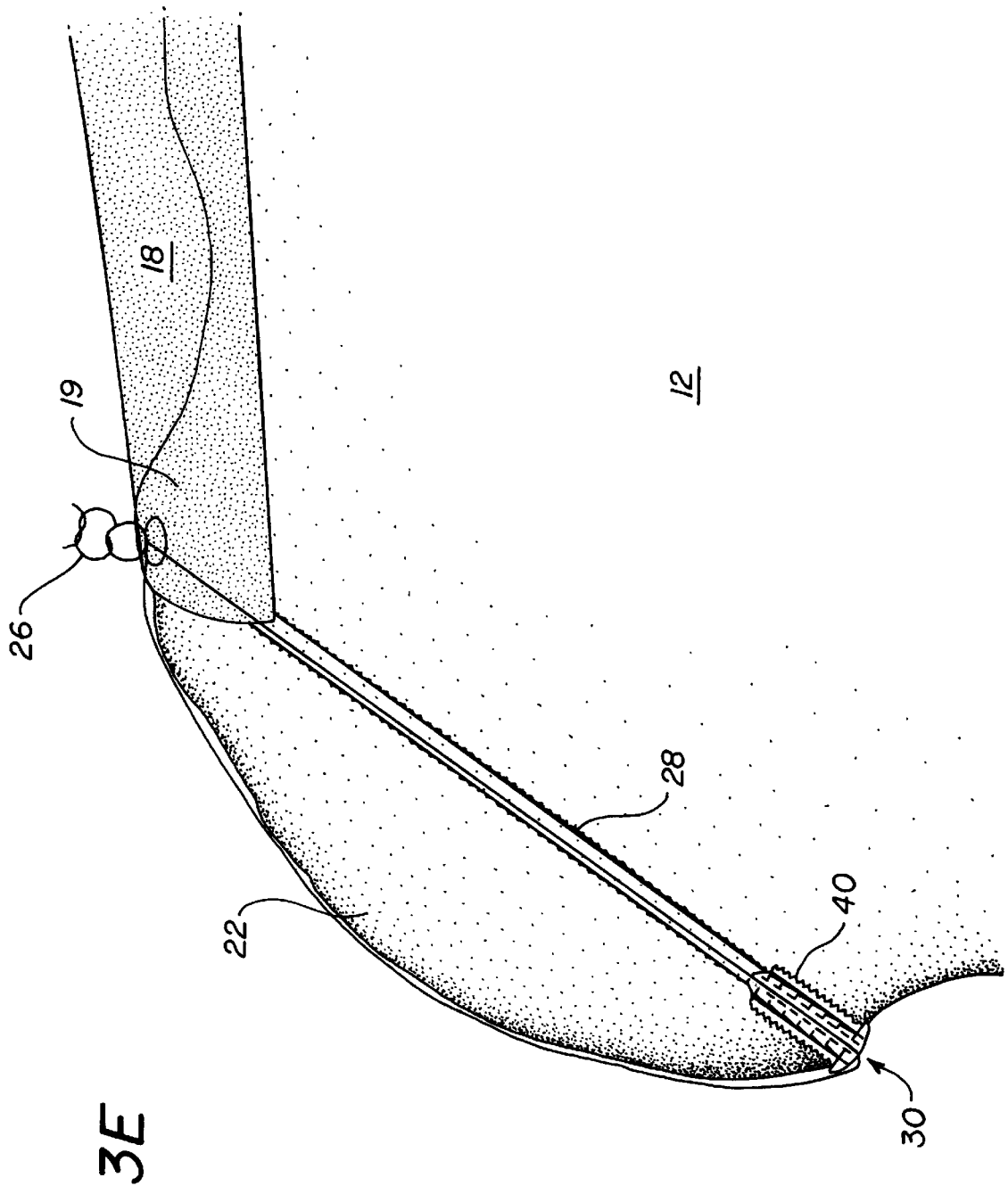

A surgical technique according to the invention proceeds in accord with conventional surgical techniques for suture rotator cuff repair. Once the transosseous tunnel 28 is drilled, however, the eyelet 40 is installed in order to reinforce the bone hole 45 and, particularly, the opening 30 at the end of transosseous tunnel 28 on the lateral cortex of the greater tuberosity 22. Particularly, as shown in FIG. 3A, the eyelet 40 is positioned in the end of the bone hole 45. As shown in FIG. 3B, the plunger 56 is used to force the insertion element 42 into the expandable member 44, thereby fixing the insertion element 42 within the expandable member 44 and fixing the expandable member 44 in a pressure fit firmly within the opening 45. As shown in FIG. 3C, once the insertion element 42 is fully inserted, the continued force of the plunger 56 causes the holding member 54 to detach from the expandable member 44 at the frangible junction 55. Once the eyelet is installed, the suture rotator cuff repair surgery is completed in the normal course, with the transosseous suture 26 being passed through the eyelet 40 and, particularly, channels 46 and 52, as shown in FIG. 4D. The completed repair, using eyelet 40, is shown in FIG. 3E.

Eyelets other than that shown in FIGS. 3A–3E may also be used to practice the invention. These are shown, for example, in FIGS. 4–7.

Referring to FIGS. 4A–4C, there is shown a threaded two-part eyelet 58 having an insertion member 60 and an expandable member 62. The eyelet is used in the manner described above, however, the insertion member 60 is screwed (rather then pushed) into the expander member 62 after the latter has been placed in the bone hole. As shown in FIGS. 4B and 4C, as the insertion element advances into the expander member, caming surfaces 63 on the insertion element 60 force wings 64 on the expander member 62 into walls of the bone hole. The expanded wings act as anchors, preventing the assembled unit (as shown in FIG. 4C) from moving within the hole. The expander element includes a flanged head region that prevents the assembly from being driving further into the bone hole by the force of the suture (not shown). As above, both the insertion member 60 and expander element 62 are cannulated in order to permit the suture to pass therethrough.

Figure 5A:
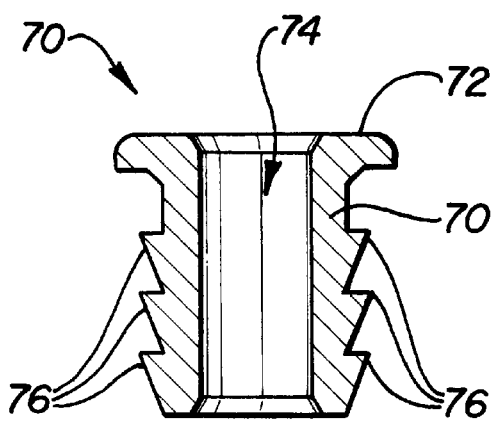
Figure 5B:
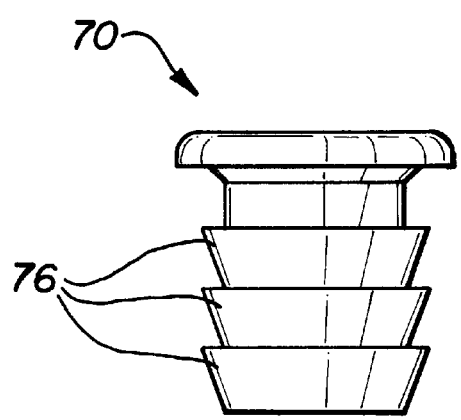
Figure 5C:
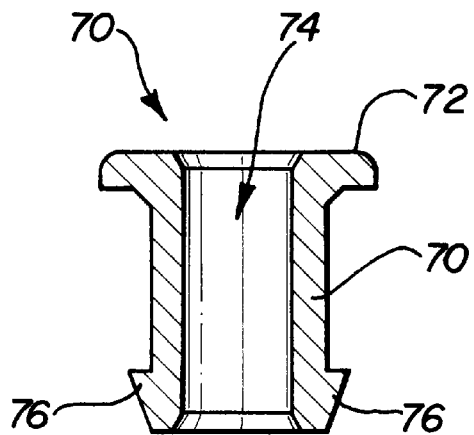
Figure 5D:
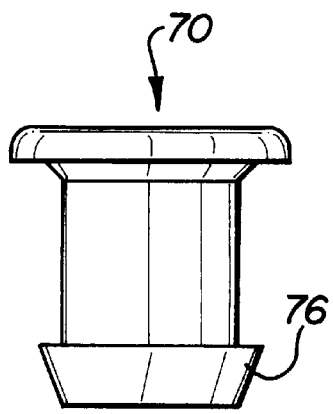

FIGS. 5A–5D show one-piece eyelets 70 according to the invention. Referring to FIGS. 5A and 5C, each eyelet 70 includes a head 72 to prevent the eyelet from being driven too far into the bone hole. The eyelet 70 also includes a cannula 74 to permit passage of a suture. On the exterior surface of the body of the eyelet are one or more annular wings that anchor the eyelet within the bone hole. An embodiment with multiple such wings 76 is shown, in cross-section, in FIG. 5A and, in side view, in FIG. 5B. An embodiment with a single such wing 76 is shown, in cross-section in FIG. 5C and, in side view, in FIG. 5D. The wings 76 are flexed or compressed inwardly on insertion of the eyelet 70 into the bone hole. Once inserted in the bone hole, the resiliency of the wings forces them back to the expanded state whence they anchor the eyelet 70.

Figure 6:
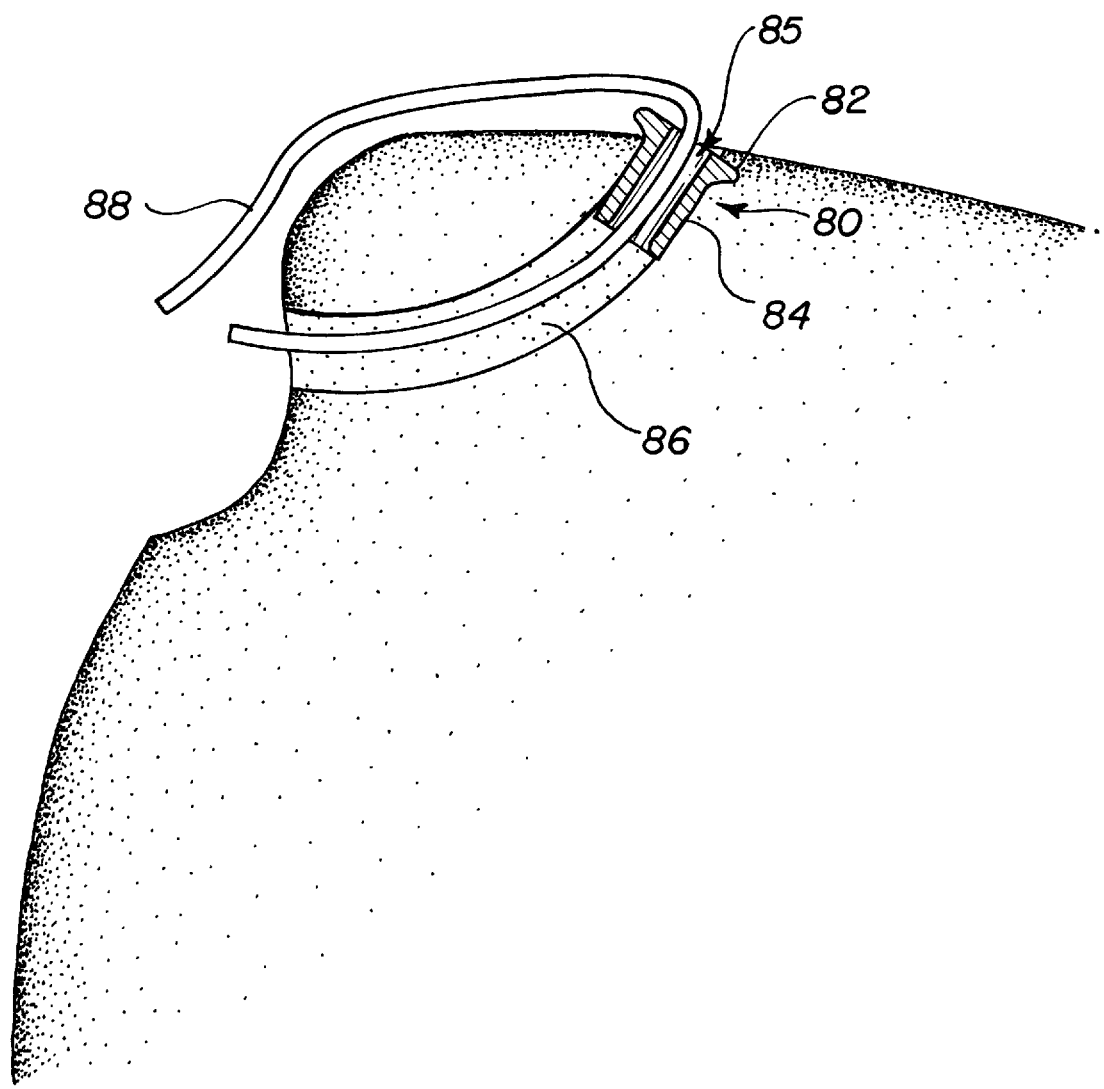

FIG. 6 shows another one-piece eyelet 80 according to the invention. The eyelet 80 includes head 82, body 84 and cannula 85. The head 82 is flanged to prevent the eyelet 80 from being pushed too far into the bone hole 86 by suture 88. The cannula 85 permits passage of the suture 88 through the eyelet. Unlike eyelet 70 described above, eyelet 80 does not include wings at its distal end. Rather eyelet 80 is held by simple interference fit with the curved walls of hole 86, as shown.

Figure 7:
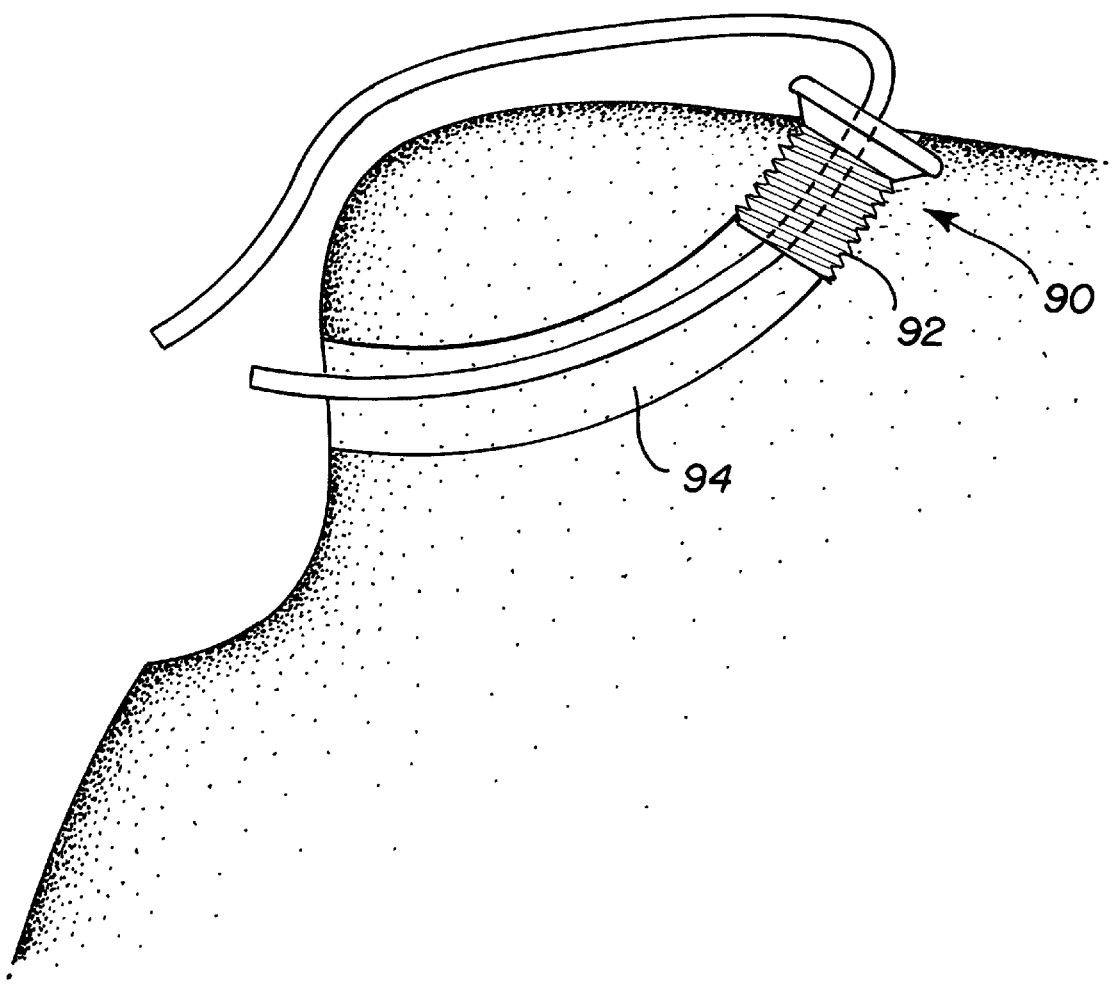

FIG. 7 shows yet another one-piece eyelet 90 constructed like eyelet 80, except for inclusion of spiral threads 92 on the body of the eyelet. These threads permit eyelet 90 to be screwed into bone hole 94, as shown.

The eyelets shown in FIGS. 4–7 are comprised of a biocompatible materials such as implant grade high density polyethylene, low density polyethylene (PE 6010 and PE 2030) and polypropylene (13R9A and 23M2: all made by Rexene, Dallas, Tex.). The eyelets may also be comprised of a metal, such as, surgical implant grade stainless steel.

Described above are methods and apparatus meeting the objects set forth above. Those skilled in the art will appreciate that the illustrated embodiments are shown and described by way of example only, and that other methods and apparatus incorporating modifications therein fall within the scope of the invention. For example, in addition to rotator cuff repair, the invention can be beneficially applied in connection with other soft tissue-to-bone attachments utilizing transosseous tunnels, such as (by way of nonlimiting example) distal biceps tendon repair, scapho-lunate ligament repair and dorsal capsulodesis, DRUJ arthroplasty, reconstruction RCL/UCL of the thumb, reconstruction RCL/UCL of the fingers, repair of central siip for Boutonniere deformity of the hand, repair of terminal tendon for Mailet deformity of the hand, repair of avulsed or lacerated FDP/FDS, repair of ATF/CF ligaments to correct lateral ligamentous instability of the ankle/foot, achilles tendon repair following tear, bifurcate ligament repair to correct avultion of anterior lateral calcaneous.

In view of the foregoing, what we claim is:

1. A device for reinforcing a transosseous tunnel to prevent migration of a suture through bone at the end thereof, comprising an eyelet arranged for placement within any of (i) a bone hole forming the end of the tunnel, and (ii) an expansion of the bone hole forming the end of the tunnel, said eyelet having a channel extending therethrough and a suture extending through the channel, passing through both ends of the transosseous tunnel and forming a loop thereby.

2. A device for use in rotator cuff repair for reinforcing a transosseous tunnel to prevent migration of a suture through a humerus bone at the end of the tunnel, the device comprising an eyelet arranged for placement within any of (i) a bone hole forming the end of the tunnel, and (ii) an expansion of the bone hole forming the end of the tunnel, said eyelet having a channel extending therethrough and a suture extending through the channel, passing through both ends of the transosseous tunnel and forming a loop thereby.

3. A device according to any one of claims 1 and 2, wherein the body of the eyelet is threaded for screwing into bone wall on any of (i) an inside of the bone hole forming the end of the tunnel, and (ii) an expansion of the bone hole forming the end of the tunnel.

4. A device according to any one of claims 1 and 2, wherein the body of the eyelet is arranged for interference fit with the bone wall on any of (i) an inside of the bone hole forming the end of the tunnel, and (ii) an expansion of the bone hole forming the end of the tunnel.

5. A device according to any one of claims 1 and 2, wherein the eyelet includes a flanged head portion.

6. A device for reinforcing a transosseous tunnel to prevent migration of a suture through bone at the end thereof, comprising an eyelet arranged for placement within any of (i) a bone hole forming the end of the tunnel, and (ii) an expansion of the bone hole forming the end of the tunnel, said eyelet having a channel extending therethrough for passage of a suture and;

A. an expandable member having a channel extending therethrough; and

B. an insertion element including a channel extending therethrough, at least a portion of the insertion element including an outer diameter greater than an inner diameter of the channel at least a portion of the expandable member for expansion thereof upon engagement therewith, whereby, fully inserting the insertion element into the expandable member causes the expandable member to expand to obtain a pressure fit with the bone opening.

7. A device for use in rotator cuff repair for reinforcing a transosseous tunnel to prevent migration of a suture through humerus bone at the end of the tunnel, the device comprising an eyelet arranged for placement within any of (i) a bone hole forming the end of the tunnel, and (ii) an expansion of the bone hole forming the end of the tunnel, said eyelet having a channel extending therethrough for passage of a suture and;

A. an expandable member having a channel extending therethrough; and

B. an insertion element including a channel extending therethrough, at least a portion of the insertion element including an outer diameter greater than an inner diameter of the channel at least a portion of the expandable member for expansion thereof upon engagement therewith, whereby, fully inserting the insertion element into the expandable member causes the expandable member to expand to obtain a pressure fit with the bone opening.

8. The device according to any of claims 6 and 7, wherein the expandable member includes a flanged head that protrudes above a surface of the bone.

* * * * *